United States Patent [19]

Gray et al.

[11] 4,125,484

[45] Nov. 14, 1978

[54] TERTIARY ALCOHOLS

[75] Inventors: Robin T. Gray; Aaldert J. De Jong, both of Amsterdam, Netherlands

[73] Assignee: Shell Oil Company, Houston, Tex.

[21] Appl. No.: 771,600

[22] Filed: Feb. 24, 1977

[30] Foreign Application Priority Data

Feb. 27, 1976 [GB] United Kingdom ................. 7819/76

[51] Int. Cl.$^2$ ........................ A61K 7/46; C07C 33/02; C07C 35/02; C07C 35/22
[52] U.S. Cl. .................................. 252/522; 568/820; 568/826; 568/840; 568/878
[58] Field of Search ........... 260/617 F, 617 R, 638 G, 260/631.5, 632, 522

[56] References Cited

U.S. PATENT DOCUMENTS

| | | | |
|---|---|---|---|
| 778,243 | 12/1904 | Hofmann | 260/638 G |
| 2,414,012 | 1/1947 | Boord | 260/638 G |
| 2,867,668 | 1/1959 | Theimer | 260/631.5 |
| 2,902,495 | 9/1959 | Webb | 260/631.5 |
| 3,085,120 | 4/1963 | Seyferth et al. | 260/638 G |
| 3,390,197 | 6/1968 | Erman et al. | 260/618 F |
| 3,886,289 | 5/1975 | Sanders | 260/617 F |
| 3,887,603 | 6/1975 | Rundberg et al. | 260/638 G |
| 3,966,648 | 6/1976 | Schleppnik | 260/631.5 |

FOREIGN PATENT DOCUMENTS

| | | | |
|---|---|---|---|
| 1,082,257 | 5/1960 | Fed. Rep. of Germany | 260/617 R |
| 1,964,405 | 7/1971 | Fed. Rep. of Germany | 260/638 G |

OTHER PUBLICATIONS

Oppenlander et al., "J. Org. Chem.," vol. 21, No. 9 (1956), pp. 961-964.
Nazarov et al., "Chem. Abstracts", vol. 54 (1960), Col. 8669.
Beilstein Handbuch der Organischen Chemie, Vierfe Auflage (1965), Band VI, Erstor Tiel, pp. 341,342,348,353,364,365,366,404.

Primary Examiner—Joseph E. Evans

[57] ABSTRACT

Novel tertiary alcohols of the general formula:

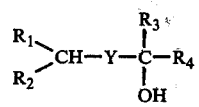

in which $R_1$ represents an alkenyl or a cycloalkyl or cycloalkenyl optionally substituted by one or more alkyl groups, $R_2$ represents hydrogen or alkyl; or $R_1$ and $R_2$, together with the carbon atom to which they are linked, from a bicyclo group optionally substituted by up to two alkyl groups; $R_3$ and $R_4$ each represents an alkyl group, and Y represents a divalent aliphatic group of up to 4 carbon atoms, are disclosed along with their use as aroma chemicals and a process for their preparation.

5 Claims, No Drawings

TERTIARY ALCOHOLS

BACKGROUND OF THE INVENTION

This invention relates to novel class of tertiary alcohols which are of interest as aroma chemicals and to a process for their preparation.

A variety of hydroxy-and carbonyl-substituted organic compounds are known in the art to possess aroma properties which are useful in the perfumery field. These compounds, which can be of natural or synthetic origin, include hydroxy-aldehydes,, esters, aldehydes, ketones and alcohols, having a broad spectrum of perfume-like odors. While, as noted, the aromas from known compounds or combinations of compounds can be quite varied, there still exists a continuing need for new compounds which accent particular fragrances or other odorant properties, especially when such compounds can be obtained from readily available synthetic sources.

SUMMARY OF THE INVENTION

A novel class of tertiary alcohols have now been found which possess distinctive aroma properties. This novel class of tertiary alcohols includes compounds of the general formula (I)

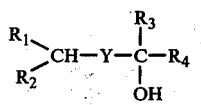
(I)

in which $R_1$ represents an alkenyl or a cycloalkyl or cycloalkenyl group of up to 8 carbon atoms optionally substituted by one or more alkyl groups; $R_2$ represents a hydrogen atom or an alkyl group, or $R_1$ and $R_2$, together with the carbon atom to which they are linked, from a bicyclo group of up to 10 carbon atoms optionally substituted by up to two alkyl groups; $R_3$ and $R_4$ each represents an alkyl group; and Y represents a divalent aliphatic group of up to 4 carbon atoms.

Also within the scope of the invention is a process by which the novel tertiary alcohols of the invention are prepared by reacting a ketone of the formula:

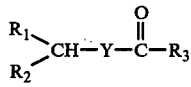

with a metal alkyl of the formula $R_4M$, wherein $R_1$, $R_2$, $R_3$, $R_4$ and Y are as defined above and M is a metal ion or the metal halide portion of a Grignard reagent, followed by hydrolysis of the adduct thus formed.

DESCRIPTION OF THE PREFERRED EMBODIMENTS

Preferred tertiary alcohols of formula (I) above are those in which $R_1$ represents a hexenyl or cyclohexenyl group substituted by one or two alkyl groups of 1 to 4 carbon atoms, for example dimethylhexenyl, methylcyclohexenyl or dimethylcyclohexenyl; $R_2$ represents a hydrogen atom or an alkyl group of 1 to 4 carbon atoms, in particular methyl, or $R_1$ and $R_2$, together with the carbon atom to which they are linked, from a bicyclo group of 7 to 9 carbon atoms, substituted by two alkyl groups each of 1 to 4 carbon atoms, for example, a dimethylbicyclo[2,2,1]heptyl, a dimethylbicyclo[3,1,1]heptyl, dimethylbicyclo[3,1,1]heptenyl or a dimethylbicyclo[3,3,1]nonenyl group; $R_3$ and $R_4$ each represents an alkyl group of 1 to 4 carbon atoms, in particular methyl; and Y represents an alkylene or alkenylene group of 1 to 3 carbon atoms, for example, methylene, propylene or propenylene.

Specific examples of preferred tertiary alcohols of formula (I) are:

5-(2,2-dimethylbicyclo[2,2,1]hepta-3-yl)-2-methylpent-3-en-2-ol 5-(6,6-dimethylbicyclo[3,1,1]hepta-2-yl)-2-methylpent-3-en-2-ol 5-(1,4-dimethylcyclohex-1-en-4-yl)-2-methylhex-3-en-2-ol 5-(1-methylcyclohex-1-en-4-yl)-2-methylhept-3-en-2-ol 2,7,11-trimethyldodeca-3,10-dien-2-ol 3-(2,5-dimethylbicyclo[3,3,1]non-2-en-8-yl)-2-methylpropan-2-ol 5-(6,6-dimethylbicyclo[3,1,1]hept-2-en-2-yl)-2-methylpentan-2-ol The tertiary alcohols of the invention may be prepared by a process which comprises reacting a ketone of formula:

(II)

wherein $R_1$, $R_2$, $R_3$ and Y are as defined for formula I above, with a metal alkyl derivative, preferably a lithium alkyl of formula $R_3Li$ or an alkyl Grignard reagent, and hydrolyzing the adduct thus formed. The process is preferably carried out in an organic solvent, for example an ether such as diethyl ether.

The ketone of formula (II) in which Y represents a propenylene group of formula $-CH_2CH=CH-$ may be obtained by a process which comprises the hydroformylation of an olefin of formula:

(III)

wherein $R_1$ and $R_2$ are as defined above, to give a monoaldehyde which is reacted with a methyl ketone of formula:

$CH_3COR_3$ (IV)

wherein $R_3$ is as defined above, in the presence of a base to give a hydroxy-ketone, which is then dehydrated to give the unsaturated ketone of formula (II).

The term "hydroformylation" is used herein to mean a reaction in which a compound containing a $>C=CH_2$ group is reacted with a mixture of hydrogen and carbon monoxide in the presence of a metal carbonyl derivative as catalyst to form a compound containing a $CH-CH_2-CHO$ grouping. The catalyst is preferably a rhodium carbonyl derivative. Particularly preferred rhodium carbonyl derivatives contain in addition to one or more carbonyl groups, a hydrido group and/or one or more phosphorus-containing ligands. The catalyst may be a homogeneous catalyst such as the compound $HRh(CO)(P(C_6H_5)_3)_3$ or a heterogeneous catalyst obtained, for example, by incorporating such a homogeneous catalyst onto a solid carrier, such as silica.

The temperature of the hydroformylation is preferably from 50° to 200° C. and the pressure up to 200 atm.

The reaction of the mono-aldehyde formed in the hydroformylation step with the methyl ketone may be carried out under the usual conditions for "mixed" aldol condensations. It is desirable to use an excess of the methyl ketone since in some cases the self-condensation of the ketone can occur. If a strong base, for example a hydroxide of an alkali or alkaline earth metal, is used as catalyst, the condensation and dehydration steps can be carried out together without isolation of the intermediate hydroxy-ketone. On the other hand, the use of weaker bases such as the carbonates of an alkali or alkaline earth metal does not bring about the subsequent elimination of water. In this case the hydroxy-ketone is dehydrated in a separate step, for example, by heating alone or in the presence of an acidic catalyst.

As mentioned above the tertiary alcohols of the invention are of interest as aroma chemicals. They may be used in ways well-known in the perfumery industry, for example as a component of perfume compositions together with other convention additives. The tertiary alcohols or perfume compositions containing them may also be used in the preparation of perfumed products such as soaps, detergents, aerosols, deodorants and cosmetic preparations. The compound 5-(6,6-dimethylbicyclo[3,1,1]hept-2-yl)-2-methylpent-3-en-2-ol is particularly preferred because of its odor of sandalwood.

The invention is illustrated further in the following Examples. The NMR spectra of the compounds were obtained at 60 MHz in deuterochloroform solution; the absorptions in ppm are quoted relative to a tetramethylsilane standard. The infrared spectra of the compounds were obtained as films between KBr plates.

EXAMPLE I (a) 6.6-Dimethylbicyclo[3,1,1]heptan-2-yl acetaldehyde was prepared by hydroformylating 6,6-dimethyl-2-methylenebicyclo[3,1,1]heptane(beta-pinene) in the presence of a rhodium carbonyl catalyst. The substituted acetaldehyde (10 g), acetone (100 g) and barium hydroxide (4.0 g) were heated together under reflux for 15 hours. The mixture was then filtered and the excess acetone was removed under reduced pressure. The residue was then fractionally distilled to give 5-(6,6-dimethylbicyclo[2,1,1]hept-2-yl)pent-3-en-2-one, b.p. 110° C. at 0.4 mm Hg.

(b) The substituted pentenone prepared as in (a) (1.0 g) was dissolved in dry diethylether (10 ml) and the solution was cooled to 0° C. A 2M solution of methyl lithium in diethyl ether (5 ml) was then added and the mixture was stirred at 20° C. for 1 hour. The mixture was cooled again to 0° C. and water (20 ml) followed by diethyl ether (10 ml) were then added. The ether phase was separated, washed and dried and the solvent was then removed under reduced pressure. Fractional distillation of the residue gave the desired unsaturated alcohol 5-(6,6-dimethylbicyclo[3,1,1]hept-2-yl)-2-methylpent-3-en-2-ol, b.p. 140° C. at 0.4 mm Hg.

N MR spectrum: 0.08 (singlet, 3 H); 1.17 (singlet, 3 H), 1.28 (singlet, 6 H); 5.50–5.65 (multiplet, 2 H)
IR spectrum: 3350 cm$^{-1}$ (OH)
Aroma: woody, like that of sandalwood.

EXAMPLES II–VII

Following procedures similar to that given in Example I, further compounds were prepared, the properties of which are set out below.

II.

5-(2,2-dimethylbicyclo[2,2,1]hept-3-yl)-2-methylpent-3-en-2-ol, b.p. 140° C. at 0.4 mm Hg.

NMR spectrum: four singlets at 0.82, 0.88, 0.93 and 0.97 (6 H); 1.30 (singlet, 6 H); 5.30–5.60 (multiplet, 2 H).
IR spectrum: 3350 cm$^{-1}$ (OH)
Aroma: weakly woody.

III.

5-(1,4-dimethylcyclohex-1-en-4-yl)-2-methylhex-3-en-2-ol, b.p. 140° C. at 0.4 mm Hg.

NMR spectrum: 0.86 (singlet, 3 H); 1.30 (singlet, 6 H); 1.67 (broad singlet, 3 H); 5.28 (multiplet, 1 H); 5.55–5.70 (multiplet, 2 H).
IR spectrum: 3350 cm$^{-1}$ (OH)
Aroma: woody

IV.

5-(1-methylcyclohex-1-en-4-yl)-2-methylhept-3-en-2-ol, b.p. 140° C. at 0.4 mm Hg.

NMR spectrum: 1.01 (broad doublet, 3 H); 1.30 (singlet, 6 H); 1.63 (broad singlet, 3 H); 5.33 (multiplet, 1 H); 5.50–5.70 (multiplet, 2 H).
IR spectrum: 3340 cm$^{-1}$ (OH)
Aroma: woody.

V. 2,7,11-trimethyldodeca-3,10-dien-2-ol, b.p. 140° C. at 0.4 mm Hg.

NMR spectrum: 1.02 (doublet, 3 H); 1.30 (singlet, 6 H); 1.60 (broad singlet, 3 H); 1.68 (broad singlet, 3 H); 4.91–5.29 (multiplet, 1 H); 5.50–5.70 (multiplet, 2 H).
IR spectrum 3340 cm$^{-1}$ (OH)
Aroma: woody.

VI.

3-(2,5-dimethylbicyclo[3,3,1]non-2-en-8-yl)-2-methylpropan-2-ol b.p. 150° C. at 0.4 mm Hg.

NMR spectrum: 0.85 ppm (singlet, 3 H); 1.22 ppm (singlet, 6 H); 5.53 ppm (multiplet, 1 H).
Aroma: camphoric woody.

VII.

5-(6,6-dimethylbicyclo[3,1,1]hepta-2-en-2-yl)-2-methylpentan-2-ol b.p. 150° C. at 0.7 mm Hg.

NMR spectrum: 0.85 (singlet, 3 H); 1.28 (singlet, 3 H); 1.20 (singlet, 6 H); 5.18 (multiplet, 1 H).
IR spectrum: 3320 cm$^{-1}$ (OH)
Aroma: floral/woody

EXAMPLE VIII

The compound of Example VII was hydrogenated in cyclohexane solution using hydrogen at a pressure of 1 atm and 10% platinum on charcoal as catalyst. The resulting product was 5-(6,6-diemthylbicyclo[3,1,1-]hept-2-yl)-2-methylpentan-2-ol.

NMR spectrum: 1.22 (singlet, 9 H); 1.02 ppm (singlet, 3 H)
Aroma: camphoric/sandalwood-like.

What is claimed is:

1. A tertiary alcohol compound of the formula:

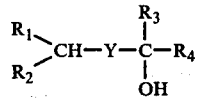

in which $R_1$ represents a dimethylhexenyl or dimethylcyclohexenyl group; $R_2$ represents a hydrogen atom or a methyl group, or $R_1$ and $R_2$, together with the carbon atom to which they are linked, form a dimethylbicyclo[2,2,1]heptyl, dimethylbicyclo[3,1,1]heptyl, dimethylbicyclo[2,1,1]heptenyl or dimethylbicyclo[3,3,1]nonenyl group; $R_3$ and $R_4$ each represents a methyl group; and Y represents a methylene, propylene or propenylene group; with the proviso that when $R_1$ is a dimethylhexenyl group, Y is a propenylene group.

2. 5-(2,2-dimethylbicyclo[2,2,1]hepta-3-yl)-2-methylpent-3-en-2-ol.

3. 5-(6,6-dimethylbicyclo[3,1,1]hept-2-yl)-2-methylpent-3-en-2-ol.

4. 5-(6,6-dimethylbicyclo[3,1,1]hepta-2-en-2-yl)-2-methylpentan-2-ol.

5. A perfume composition or a perfumed product comprising a tertiary alcohol of claim 1 together with an adjuvant therefor.

* * * * *